(12) United States Patent
Ziemek et al.

(10) Patent No.: US 11,957,387 B2
(45) Date of Patent: Apr. 16, 2024

(54) DYNAMIC STABILIZATION SYSTEMS AND ASSOCIATED METHODS

(71) Applicant: Zimmer Biomet Spine, Inc., Westminster, CO (US)

(72) Inventors: Terry Ziemek, Broomfield, CO (US); Randall G. Mast, Denver, CO (US); Allison Christine Capote, Boulder, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 365 days.

(21) Appl. No.: 16/851,713

(22) Filed: Apr. 17, 2020

(65) Prior Publication Data
US 2020/0237408 A1 Jul. 30, 2020

Related U.S. Application Data

(63) Continuation of application No. 16/116,504, filed on Aug. 29, 2018, now Pat. No. 10,653,453.
(Continued)

(51) Int. Cl.
*A61B 17/70* (2006.01)
*A61B 17/80* (2006.01)
(Continued)

(52) U.S. Cl.
CPC ...... *A61B 17/7044* (2013.01); *A61B 17/7008* (2013.01); *A61B 17/7022* (2013.01);
(Continued)

(58) Field of Classification Search
CPC ............ A61B 17/7044; A61B 17/7058; A61B 17/7076; A61B 17/7082; A61B 17/0642
See application file for complete search history.

(56) References Cited

U.S. PATENT DOCUMENTS 5,810,816 A * 9/1998 Roussouly ......... A61B 17/7044
606/301
5,899,905 A * 5/1999 Errico ................ A61B 17/7032
606/267
(Continued)

FOREIGN PATENT DOCUMENTS

EP 1997448 A1 12/2008
EP 2266483 A1 12/2010
(Continued)

OTHER PUBLICATIONS

"Australian Application Serial No. 2018324017, First Examination Report dated Jun. 10, 2020", 4 pages.
(Continued)

*Primary Examiner* — Julianna N Harvey
(74) *Attorney, Agent, or Firm* — Sheridan Ross P.C.

(57) ABSTRACT

Implementations described herein include a system that may include a deliver device, an annular anchor and an implant. The delivery device may include a distal end, a proximal and a lumen extending from the distal end to the proximal end. The annular anchor may be removably coupleable to the distal end of the delivery device. The annular anchor may be implantable at a target site in a patient via manipulation of the delivery device. The delivery device may be extendable outside the patient when the anchor is implanted at the target site. The implant may be deliverable through the delivery device to the target delivery site and implantable through the annular anchor. The delivery device may be coupled to the annular anchor to control a trajectory of the implant to the target site.

9 Claims, 15 Drawing Sheets

Related U.S. Application Data

(60) Provisional application No. 62/551,845, filed on Aug. 30, 2017.

(51) Int. Cl.
*A61B 17/02* (2006.01)
*A61B 17/064* (2006.01)
*A61F 2/44* (2006.01)

(52) U.S. Cl.
CPC ...... *A61B 17/7031* (2013.01); *A61B 17/7083* (2013.01); *A61B 17/809* (2013.01); *A61B 17/0206* (2013.01); *A61B 2017/0648* (2013.01); *A61B 17/7074* (2013.01); *A61B 17/7076* (2013.01); *A61B 17/7077* (2013.01); *A61B 17/708* (2013.01); *A61B 17/7085* (2013.01); *A61B 17/7091* (2013.01); *A61B 17/808* (2013.01); *A61F 2/44* (2013.01)

(56) References Cited

U.S. PATENT DOCUMENTS

| | | | |
|---|---|---|---|
| 6,533,787 | B1 | 3/2003 | Lenke et al. |
| 7,909,826 | B2 | 3/2011 | Serhan et al. |
| 10,653,453 | B2 | 5/2020 | Ziemek et al. |
| 2006/0074445 | A1 | 4/2006 | Gerber et al. |
| 2006/0217715 | A1* | 9/2006 | Serhan ............ A61B 17/701 606/86 A |
| 2008/0086131 | A1* | 4/2008 | Daly ............ A61B 17/7032 606/103 |
| 2009/0228053 | A1* | 9/2009 | Kolb ............ A61B 17/7076 606/151 |
| 2010/0106195 | A1* | 4/2010 | Serhan ............ A61B 17/92 606/279 |
| 2011/0190821 | A1* | 8/2011 | Chin ............ A61B 17/864 606/264 |
| 2013/0085536 | A1* | 4/2013 | Biedermann ...... A61B 17/7076 606/328 |
| 2015/0313659 | A1* | 11/2015 | Miyawaki ........ A61B 17/0642 606/303 |
| 2017/0049481 | A1* | 2/2017 | Faulhaber .......... A61B 17/7082 |
| 2018/0125535 | A1* | 5/2018 | Faulhaber .......... A61B 17/1671 |
| 2018/0271566 | A1 | 9/2018 | Fischer et al. |
| 2019/0059949 | A1 | 2/2019 | Ziemek et al. |
| 2019/0254730 | A1* | 8/2019 | Rohlfing .......... A61B 17/8888 |

FOREIGN PATENT DOCUMENTS

| | | |
|---|---|---|
| WO | WO-2007146032 A2 | 12/2007 |
| WO | WO-2019046443 A1 | 3/2019 |

OTHER PUBLICATIONS

"U.S. Appl. No. 16/116,504, Non Final Office Action dated Oct. 3, 2019", 7 pgs.

"U.S. Appl. No. 16/116,504, Notice of Allowance dated Feb. 18, 2020", 5 pgs.

"U.S. Appl. No. 16/116,504, Response filed Jan. 2, 2020 to Non Final Office Action dated Oct. 3, 2019", 8 pgs.

"International Application Serial No. PCT/US2018/048570, International Preliminary Report on Patentability dated Mar. 12, 2020", 9 pgs.

"International Application Serial No. PCT/US2018/048570, International Search Report dated Jan. 3, 2019", 6 pgs.

"International Application Serial No. PCT/US2018/048570, Written Opinion dated Jan. 3, 2019", 7 pgs.

U.S. Appl. No. 16/116,504, filed Aug. 29, 2018, Dynamic Stabilization Systems and Associated Methods.

Official Action for Canada Patent Application No. 3,072,758, dated Aug. 16, 2021 3 pages.

Official Action for Canada Patent Application No. 3,072,758, dated May 9, 2022 3 pages.

Notice of Allowance for Canada Patent Application No. 3,072,758, dated Apr. 14, 2023 1 page.

* cited by examiner

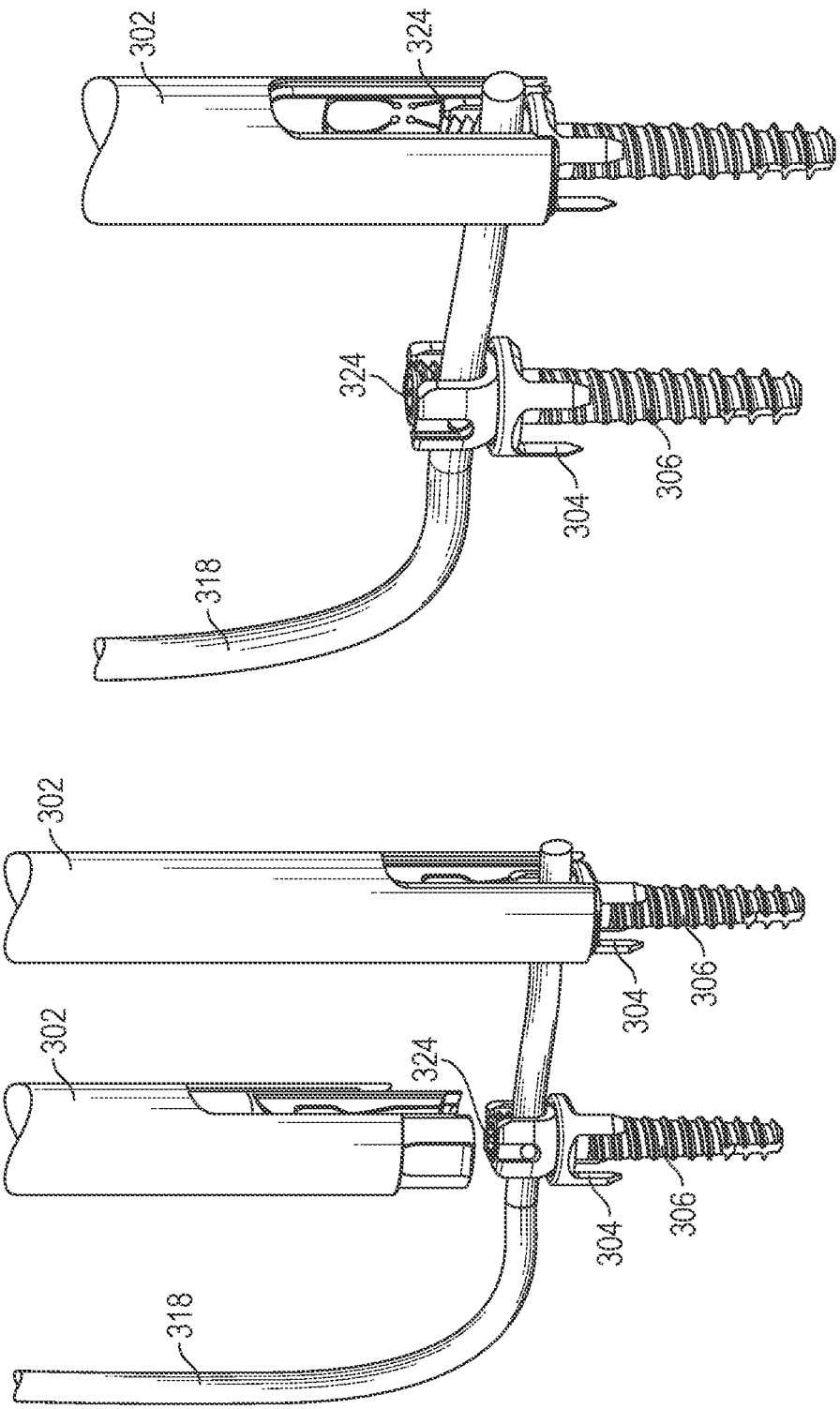

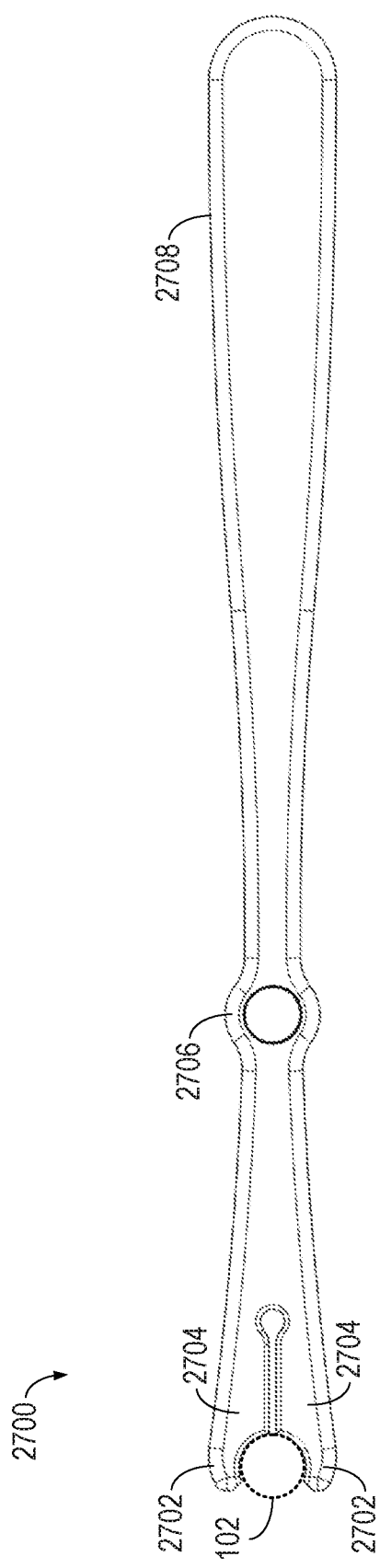

DYNAMIC STABILIZATION SYSTEMS AND ASSOCIATED METHODS

CROSS-REFERENCE TO RELATED APPLICATION

This application is a continuation of U.S. application Ser. No. 16/116,504, filed Aug. 29, 2018, which claims the benefit of U.S. Provisional Application No. 62/551,845, filed Aug. 30, 2017, which is hereby incorporated by reference in its entirety.

BACKGROUND

Dynamic stabilization techniques, such as vertebral body tethering, are used in spinal treatment procedures for juveniles to permit enhanced mobility of the spine while also providing sufficient counter loading of a spinal curvature to effect treatment through bone growth modulation, particularly during times of rapid growth. Such dynamic stabilization systems can include pedicle screws installed in adjacent vertebrae of the spine and a flexible cord secured to the heads of the pedicle screws by set screws, with the cord under tension between pedicle screws.

SUMMARY

The present inventors have recognized, among other things, a benefit in improving patient recovery and/or outcomes by minimizing the soft tissue that is displaced, damaged or otherwise affected during surgery, including, for example, the size and severity of the incisions or the need to retract tissue from a surgical site. The present inventors have also recognized a benefit in improving patient outcomes by optimizing the placement of pedicle screws while minimizing tissue displacement.

Various methods, devices, systems, and embodiments can include an easily repositionable anchor that can control the trajectory of an implant, such as a pedicle screw, via a coupled delivery device. The delivery device can accommodate delivery of multiple constructs of the system, such as an anchor, an awl, a tap, and the implant. Accordingly, the present disclosure provides for a system that can include a delivery device, an annular anchor, and an implant. The delivery device can include a distal end, a proximal end, and a lumen extending from the distal end to the proximal end. The annular anchor can be removably coupleable to the distal end of the delivery device. The anchor can be implantable at a target site in a patient via the delivery device. The delivery device can be extendable outside of the patient when the anchor is implanted at the target site. The implant can be deliverable to the target site and implantable through the annular anchor. The delivery device can be removable from the annular anchor subsequent to implantation of the implant.

In another embodiment, the present disclosure provides for a method including removably coupling a delivery device to an anchor, delivering an implant through the delivery device so that placement of the anchor controls the trajectory of the implant, securing the implant to underlying tissue, and decoupling the delivery device from the annular anchor and removing the delivery device over the implant.

This Summary is intended to provide an overview of subject matter of the present patent application. It is not intended to provide an exclusive or exhaustive explanation of the disclosure. The Detailed Description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 21 is a perspective view of the system as used to deliver multiple implants, in accordance with some embodiments.

FIG. 22 is a perspective view of the system as used to deliver multiple implants, in accordance with some embodiments.

FIG. 27 is a top view of an example of a handle suitable for use with any of the delivery devices of FIGS. 1-26.

DETAILED DESCRIPTION

A system and a method can control the trajectory of a second, more invasive, implant with a first, less invasive, implant operably coupled to a delivery device. A system can include an anchor that is removably coupleable to a delivery device in order to control the trajectory of a bone screw (e.g., second implant). The anchor can be easily repositioned to ensure optimal placement. The delivery device can accommodate an awl and a tap, as well as delivery of the anchor and the bone screw. Such systems and methods can improve patient recovery by, for example, minimizing soft tissue that is displaced or affected by the surgery. Such systems and methods can also improve patient outcomes by optimizing placement of bone screws while minimizing tissue displacement.

FIGS. 1-7 show an example of a system 100 that can control the trajectory of a second, more invasive, implant with a first, less invasive, implant operably coupled to a delivery device, in accordance with some examples. Using the system 100 to deliver an implant, such as a bone screw, can help prevent the implant from damaging surrounding tissue as the implant is delivered to its target site in the patient. The configuration of FIGS. 1-7 is but one example of such a system; other configurations can also be used.

Figures 1, 2, 3:
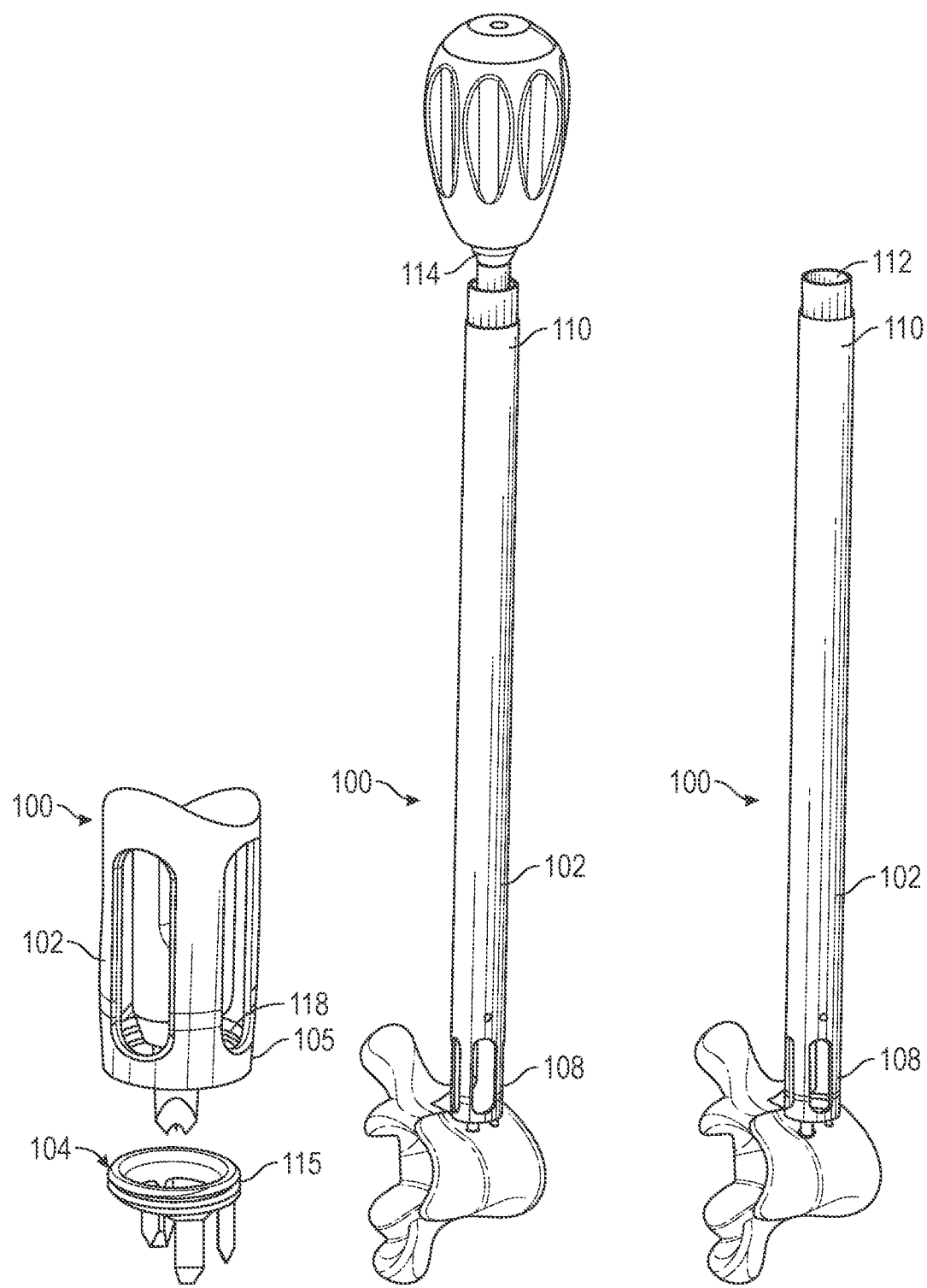
FIG. 1 is partial perspective view of a first embodiment of a system, in accordance with some embodiments.
FIG. 2 is a perspective view of the embodiment of FIG. 1 during anchor insertion with an awl.
FIG. 3 is a perspective view of the embodiment of FIG. 1 during anchor insertion without an awl.

The system 100 can include a delivery device 102, an annular anchor 104, and an implant 106 (see FIG. 5), The delivery device 102 can include a distal end 108, a proximal end 110, and a lumen 112 extending from the distal end to the proximal end. The annular anchor 104 can be removably coupleable to the distal end 108 of the delivery device 102. The annular anchor 104 can include a bone staple or a washer with spikes extending from its distal end. In one example, the annular anchor 104 can have a proximal threaded end 116 that is threadably engageable with a distal thread 118 disposed on the distal end 108 of the delivery device 102. The anchor 104 can be implanted at a target site in a patient via the delivery device 102. In operation, the annular anchor 104 is coupled to the distal end 108 of the delivery device 102 and guided to a selected vertebral body for implantation via a small incision in a minimally invasive manner. The anchor 104 can be implanted with an awl 114 as shown in FIG. 2 to create or enlarge a hole in the bone tissue or without the use of an awl as shown in FIG. 3. The awl 114 can facilitate centering the anchor 104 as it contacts the bone prior to anchor insertion and, additionally or alternatively, can add stability to the delivery device 102, The above sequence of steps can be performed in the recited or in a different order as a skilled artisan would appreciate in light of the present disclosure. Subsequent to implantation, optimal placement of the annular anchor 104 can be confirmed via fluoroscopy and, if desired, the annular anchor 104 can be repositioned to ensure the subsequent optimal placement of the implant 106 through the opening defined by the annular anchor 104 via tines engageable with underlying bone tissue. The delivery device 102 can be extendable outside of the patient when the anchor 104 is implanted at the target site to enable minimally invasive delivery and implantation of a second implant, such as a bone screw.

Figures 4, 5:
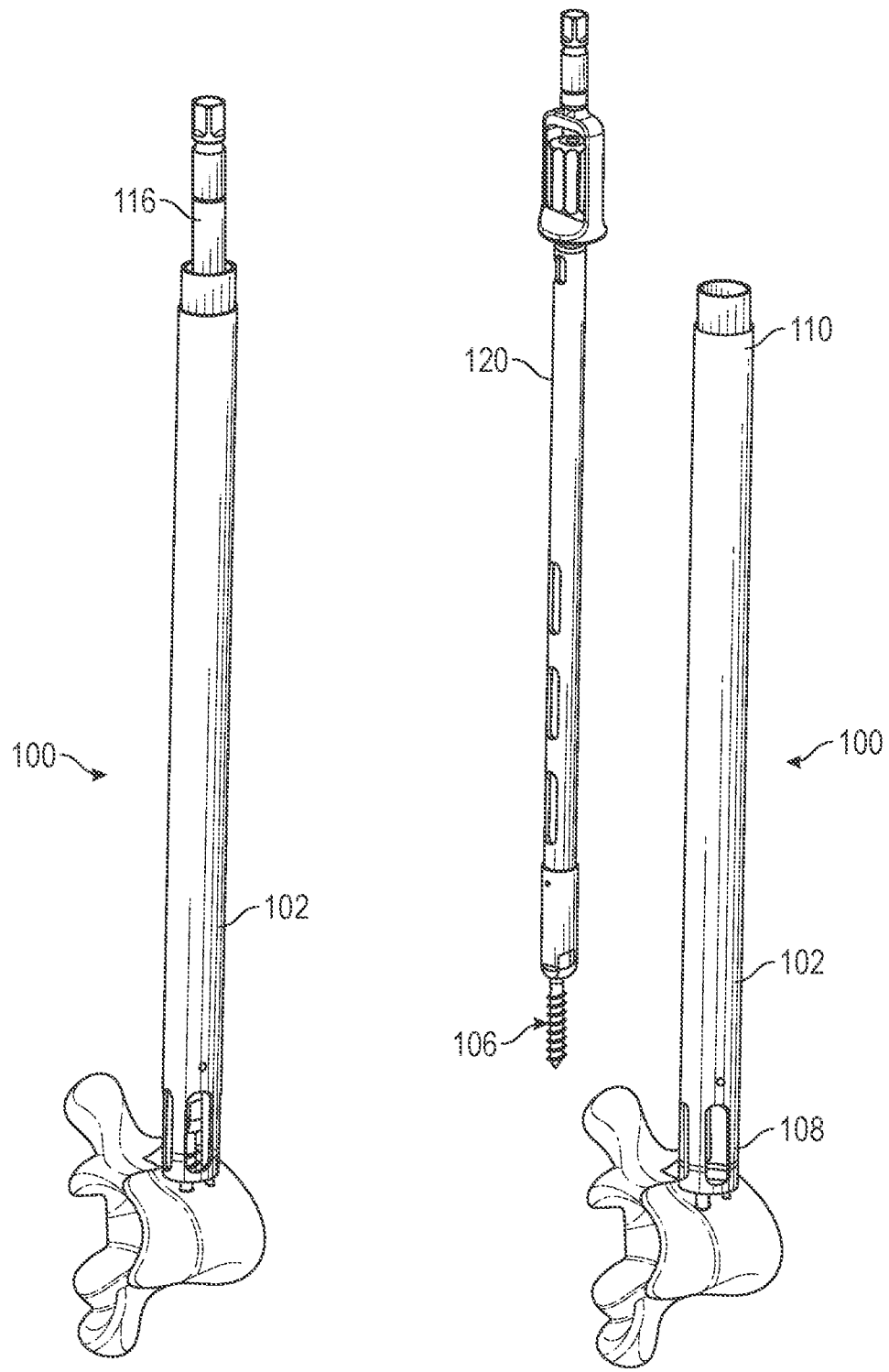
FIG. 4 is a perspective view of the embodiment of FIG. 1 during a surgical step subsequent to anchor insertion but prior to implant insertion.
FIG. 5 is a perspective view of the embodiment of FIG. 1 with an implant insertion tool.
Figure 6:
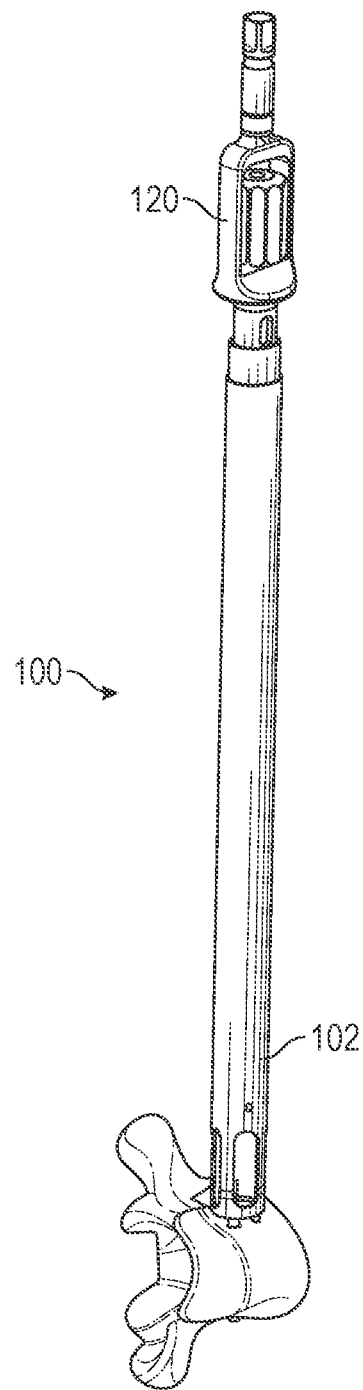
FIG. 6 is a perspective view of the embodiment of FIG. 1 during implant insertion with an implant insertion tool.
Figure 7:
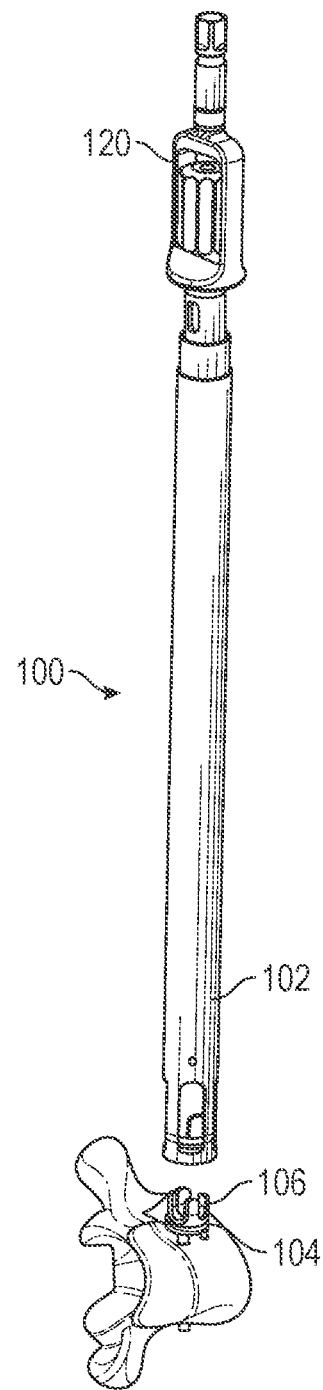
FIG. 7 is a perspective view of the embodiment of FIG. 1 after implant insertion and with the delivery device decoupled from the anchor.
Figure 8:
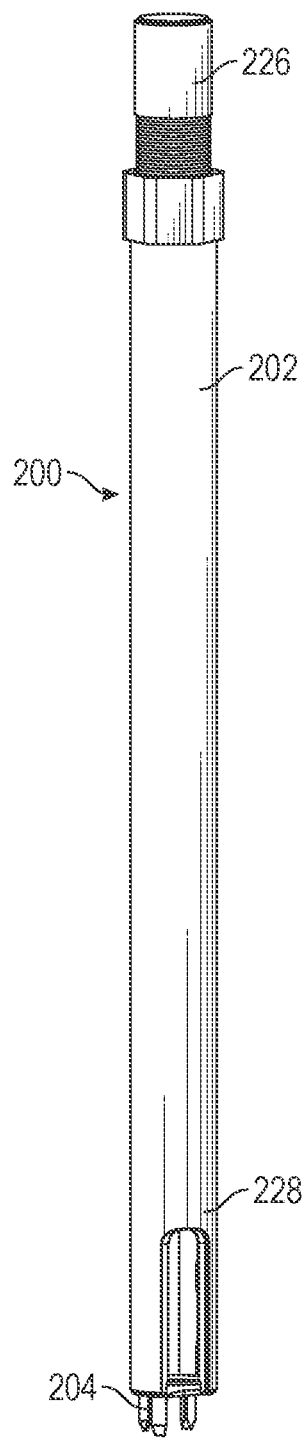
FIG. 8 is a perspective view of another embodiment of a system, in accordance with some embodiments.
Figures 9, 10:
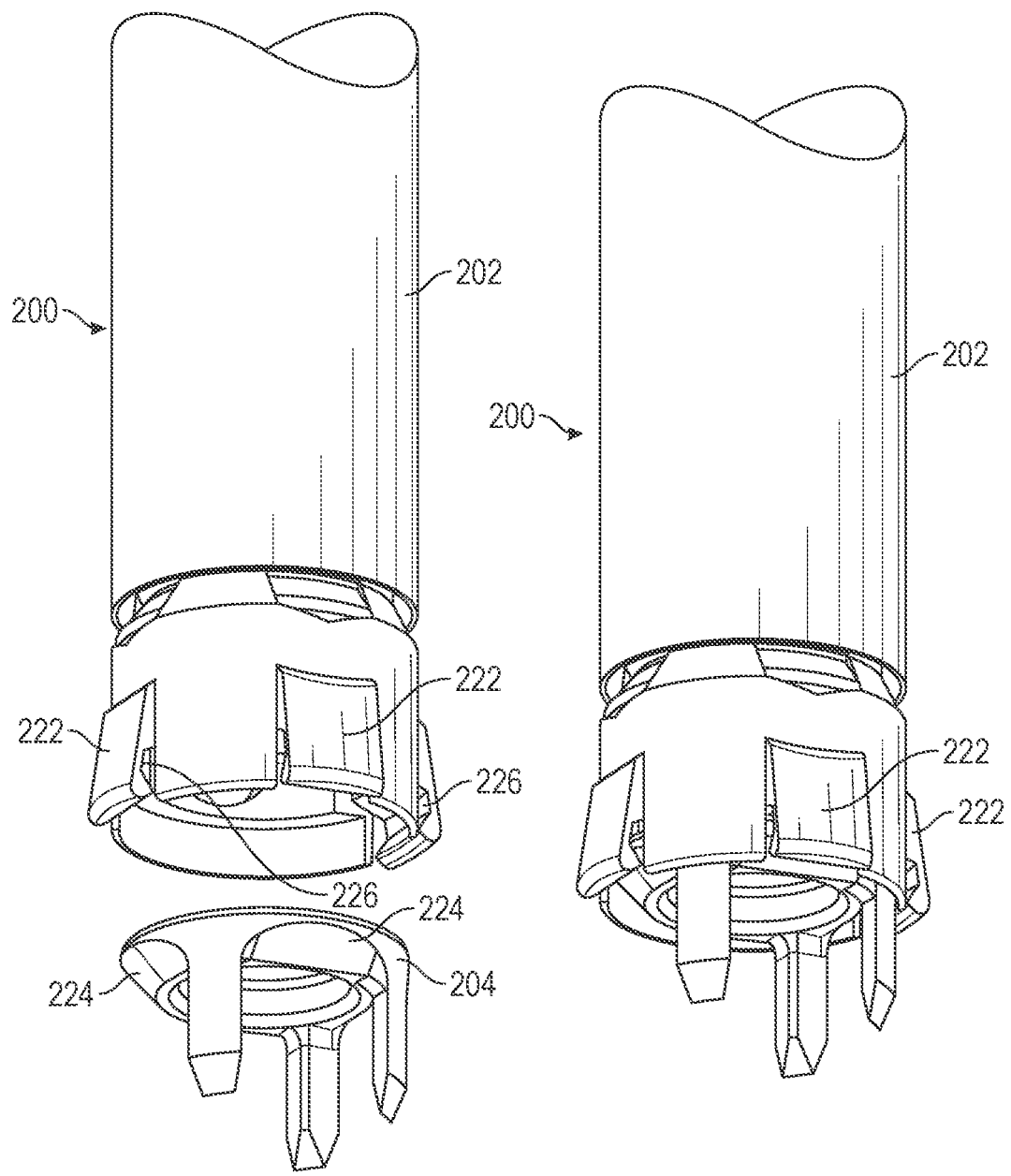
FIG. 9 is a partial perspective view of the embodiment of FIG. 8 with the delivery device in the process of engaging the anchor, in accordance with some embodiments.
FIG. 10 is a partial perspective view of the embodiment of FIG. 8 with the delivery device partially engaged with the anchor, in accordance with some embodiments.
Figures 11, 12:
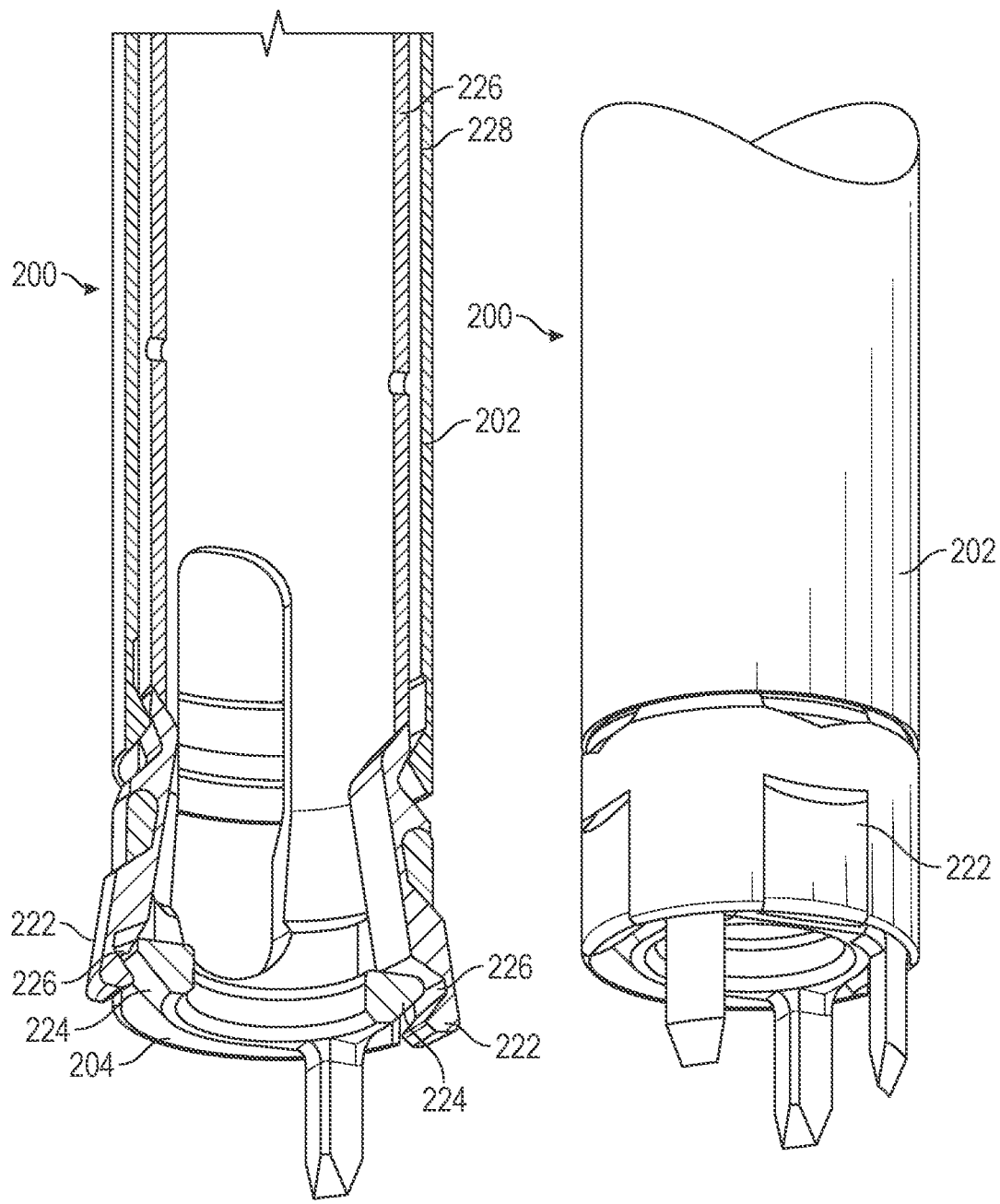
FIG. 11 is a cross-sectional view of the embodiment of FIG. 10.
FIG. 12 is a partial perspective view of the embodiment of FIG. 8 with the delivery device engaged with the anchor, in accordance with some embodiments.
Figure 13:
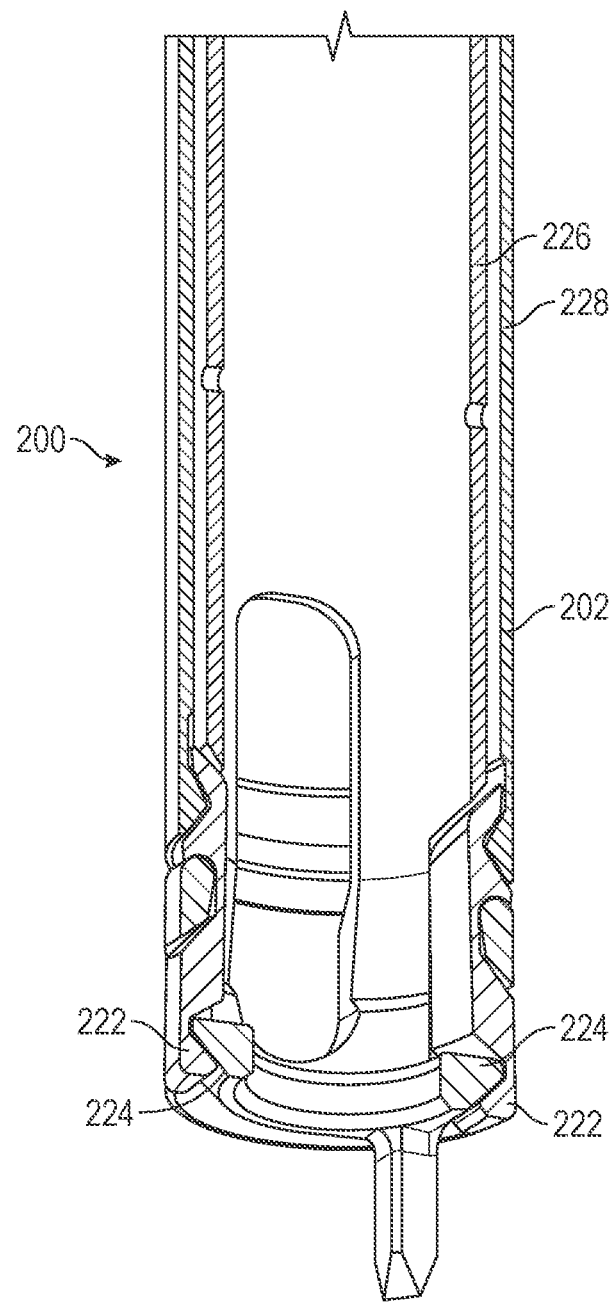
FIG. 13 is a cross-sectional view of the embodiment of FIG. 12.

Upon implantation of the anchor 104 at the target site and as shown in FIG. 4, additional tools 116 such as, for example and without limitation, a screw tap, pedicle sounder with depth gauge, or the like can be used to prepare the target site for the implant 106.

The implant 106 can be deliverable to the target site via the delivery device 102 and implantable through the annular anchor 104, which remains embedded in the target site and coupled to the distal end 108 of the delivery device. Here, the implant 106 can be coupled to a driver 120 and inserted through the lumen 112 of the delivery device 102 and the opening defined by the annular anchor 104, then implanted in the underlying bone. In this way, the trajectory of the implant 106 can be controlled to avoid unnecessary tissue displacement and the ultimate position of the implant 106 can be controlled via prior placement of the anchor 104. In an additional or alternative example, a power tool can be used to actuate the driver 120 as the delivery device 102 enhances stability of the driver 120. By way of example only, the anchor 104 and delivery device 102 may provide guidance to a powered tool, such as a hand held powered driver that may engage driver 120 for powered driving implant 106. Some health care practitioners may be hesitant to use a powered tool, which may have advantages, such as shortened surgical times and less stress on the health care practitioner's wrists and other joints. One reason for this hesitancy to utilize a powered tool for driving implants may be concern regarding driving the implant in an incorrect direction or the power tool causing the implant to skip along the bone. In this embodiment, the anchor 104 and the delivery device 102 may assist in maintaining a more accurate direction or trajectory of the implant 106 as it is being driven with a powered instrument and may secure against movement of the implant 106 from the original site during placement. The above sequence of steps can be performed in the recited or in a different order as a skilled artisan would appreciate in light of the present disclosure. The implant 106 can be a bone screw and, more particularly, can be a pedicle screw. The delivery device 102 can be uncoupled from the annular anchor 104 subsequent to implantation of the implant 106 by, for example and without limitation, unscrewing the distal thread 118 of the delivery device 102 from the proximal threaded end 115 of the annular anchor 104. Additional implants can be placed in a similar manner in adjacent vertebrae along the length of the desired construct.

Once all implants 106 are placed and proper positioning of each implant 106 is confirmed, a tether can be directed into a receiving channel defined in the head of a first implant 106. A set screw can be placed in the head of the first implant 106, securing the tether from further movement. The tether can then be placed into the receiving channel of each head of each remaining implant. Prior to securing the tether with set screws in each of the remaining implants, a tensioning instrument can be used to tension the tether. After reduction of the spinal curvature through tensioning, translation, and compression; the set screws can be placed and tightened to effect treatment of the spine.

FIGS. 8-13 show another example of a system 200 that can control the trajectory of a second, more invasive, implant with a first, less invasive, implant operably coupled to a delivery device; in accordance with some examples. Using the system 200 to deliver an implant, such as a bone screw, can help prevent the implant from damaging surrounding tissue as the implant is delivered to its target site in the patient. The configuration of FIGS. 8-13 is but another example of such a system; other configurations can also be used.

The system 200 can include delivery device 202, anchor 204, and an implant (not shown). The delivery device 202 can be removably coupleable to an annular anchor 204 via a plurality of biasable arms 222. At least a portion of the circumference of the annular anchor 204 includes a chamfered lip 224 extending inwardly from a proximal to a distal end of an annular portion of the annular anchor 204. The plurality of biasable arms 222 can each have an interior surface having a groove 226 for engaging the chamfered lip 224 of the annular anchor 104. In one example, the delivery device 202 can include an inner sheath 226 having the plurality of biasable arms 222 disposed at a distal end thereof and an outer sheath 228 that is advanceable over the inner sheath 226 to bias the biasable arms 222 to engage the annular anchor 204 and retractable over the inner sheath 226 to allow the biasable arms 222 to expand, thereby releasing the annular implant 204. Upon implantation of the annular anchor 104 and the implant (not shown), the biasable arms can be expanded to release the delivery device 202 from the annular anchor 204.

FIGS. 14-22 show another example of a system 300 that can control the trajectory of a second, more invasive, implant with a first, less invasive, implant operably coupled to a delivery device; in accordance with some examples. Using the system 300 to deliver an implant, such as a bone screw, can help prevent the implant from damaging surrounding tissue as the implant is delivered to its target site in the patient. The configuration of FIGS. 14-22 is but another example of such a system; other configurations can also be used. The system 300 of FIGS. 14-22 can be implemented alone, or with either or both of the systems 100 and 200.

Figure 14:
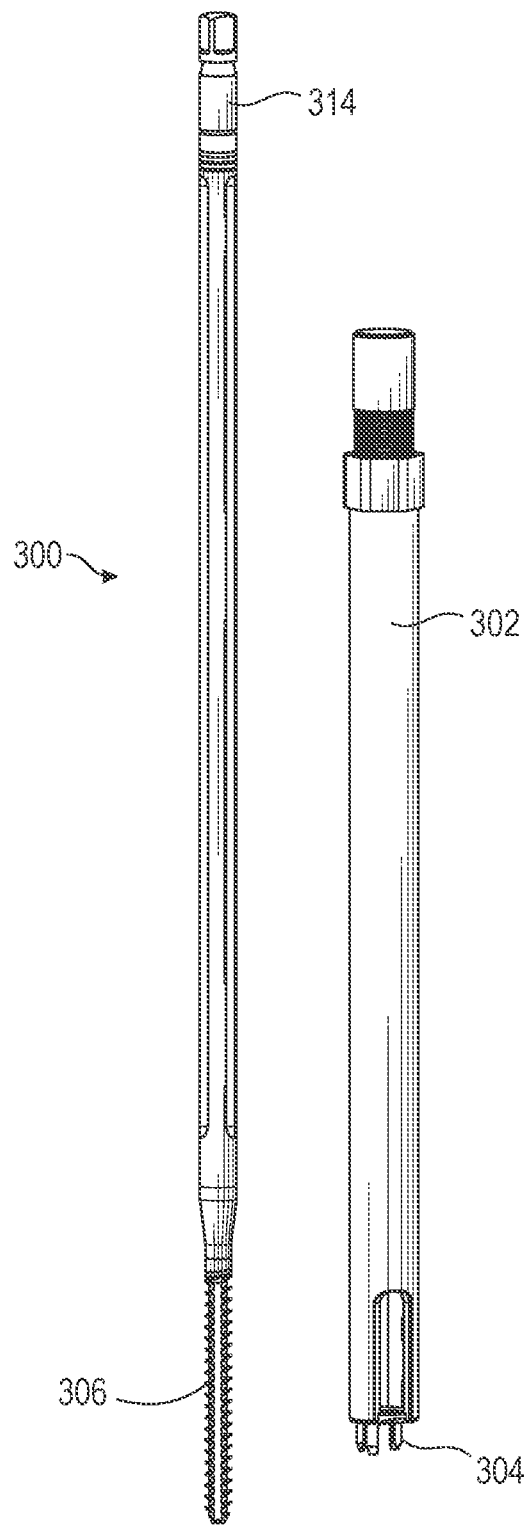
FIG. 14 is a perspective view of a system including a tap or awl, in accordance with some embodiments.
Figures 15, 16:
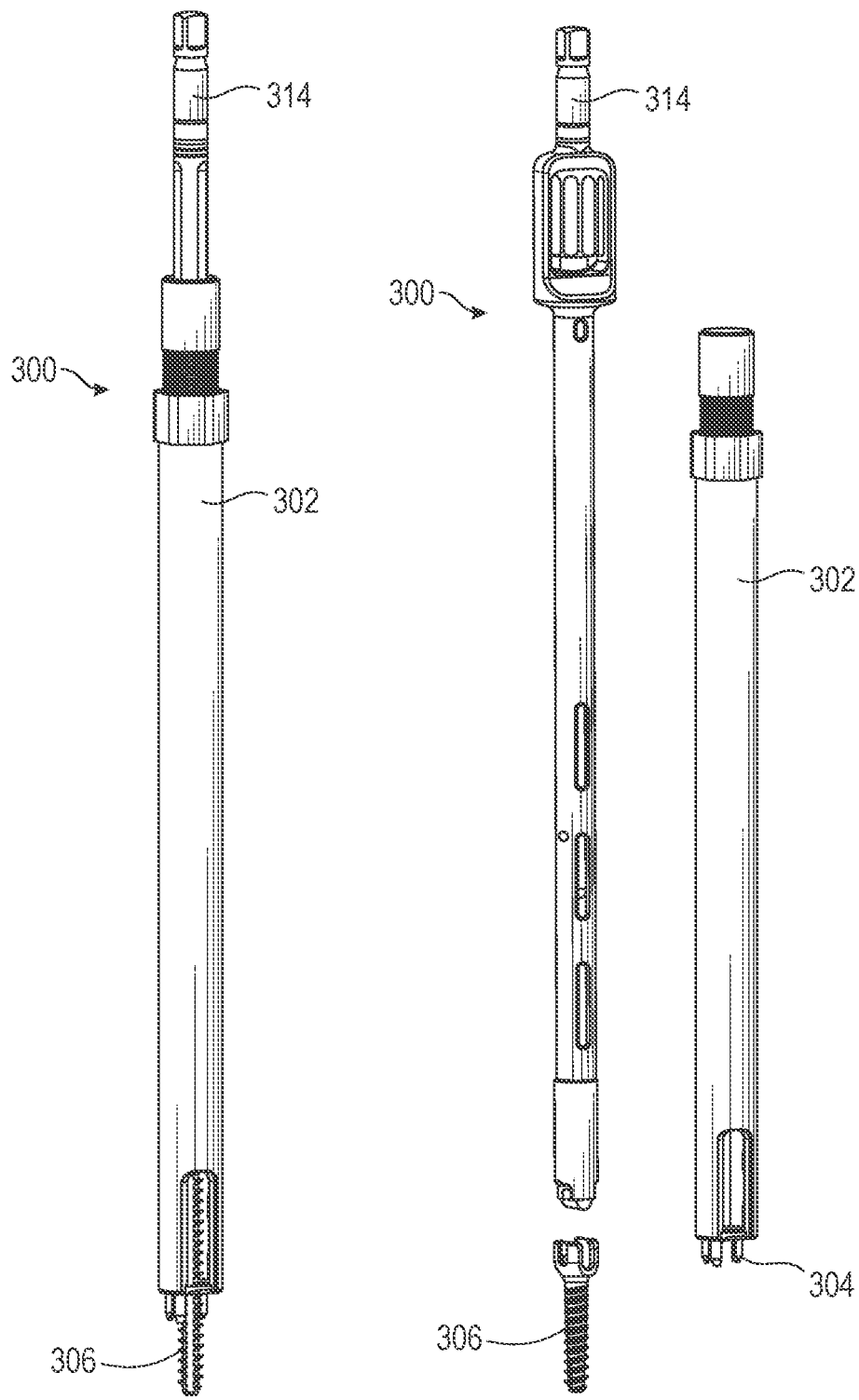
FIG. 15 is a perspective view of a system including a tap or an awl extending through the delivery device, in accordance with some embodiments.
FIG. 16 is a perspective view of a system including an implant inserter and an implant, in accordance with some embodiments.
Figure 17A:
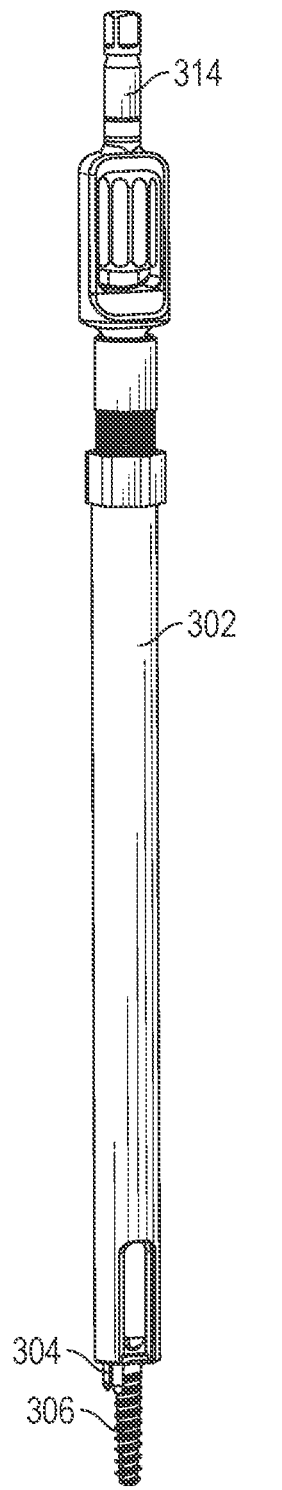
FIG. 17A is a perspective view of a system including the implant inserter extending through the delivery device
Figure 17B:
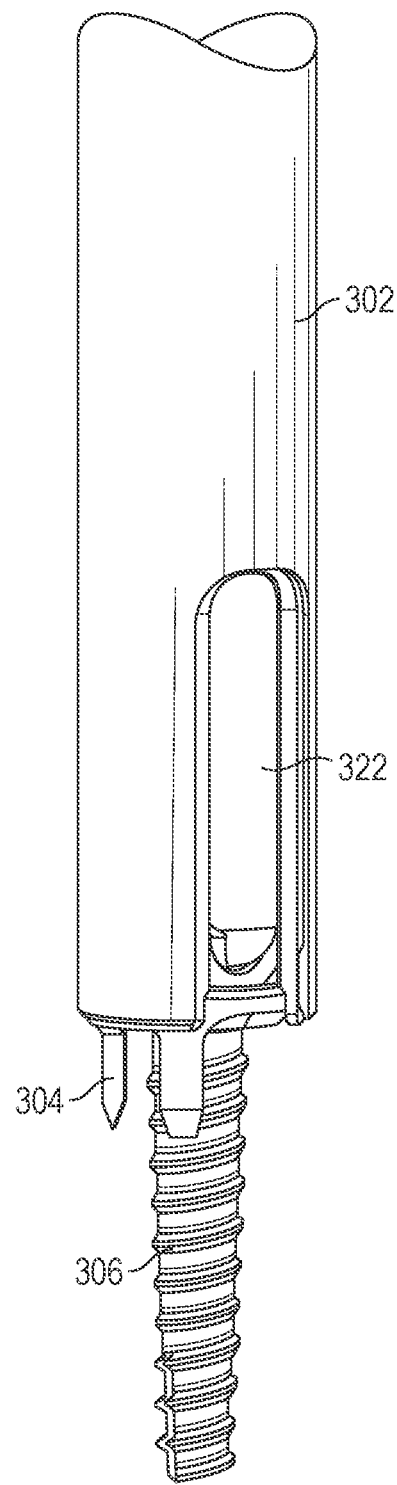
FIG. 17B is a partial perspective view of the distal end of the system of FIG. 17A.
Figure 18:
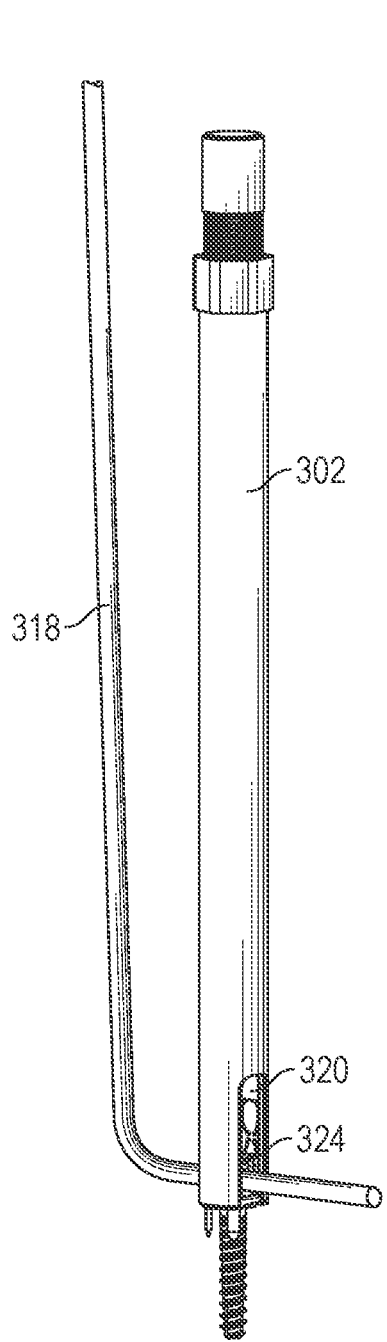
FIG. 18 is a perspective view of a system having a cord extending through the implant and delivery device, in accordance with some embodiments.
Figure 19:
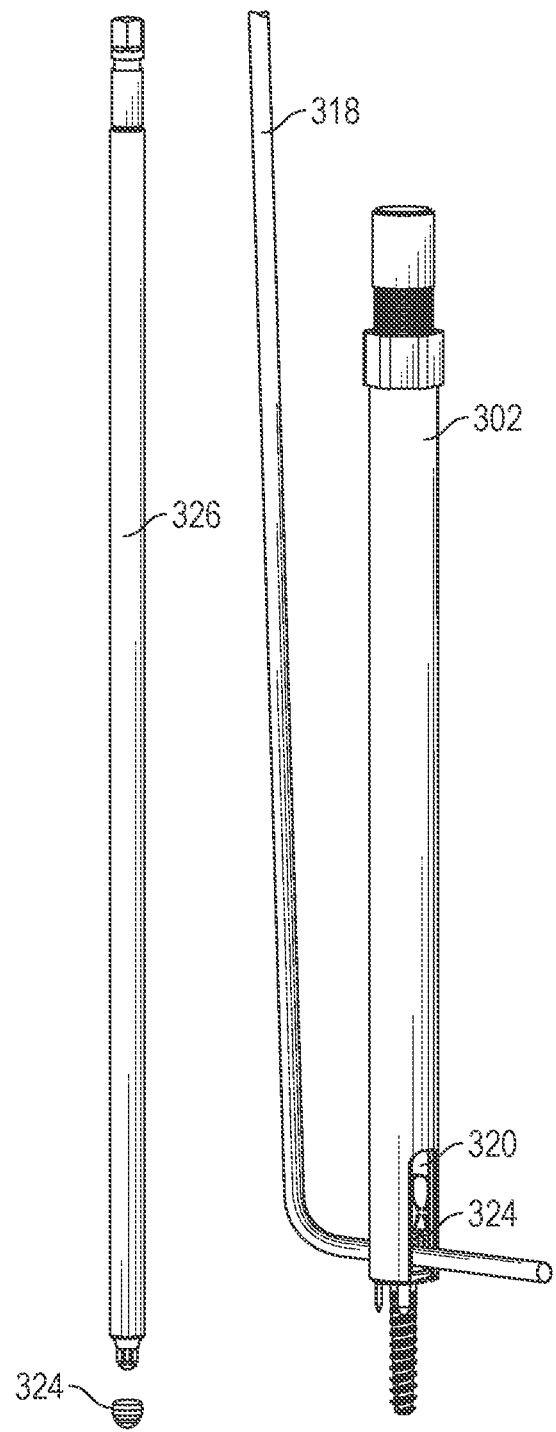
FIG. 19 is a perspective view of a system including a set screw inserter and a set screw, in accordance with some embodiments.
Figures 20A, 20B:
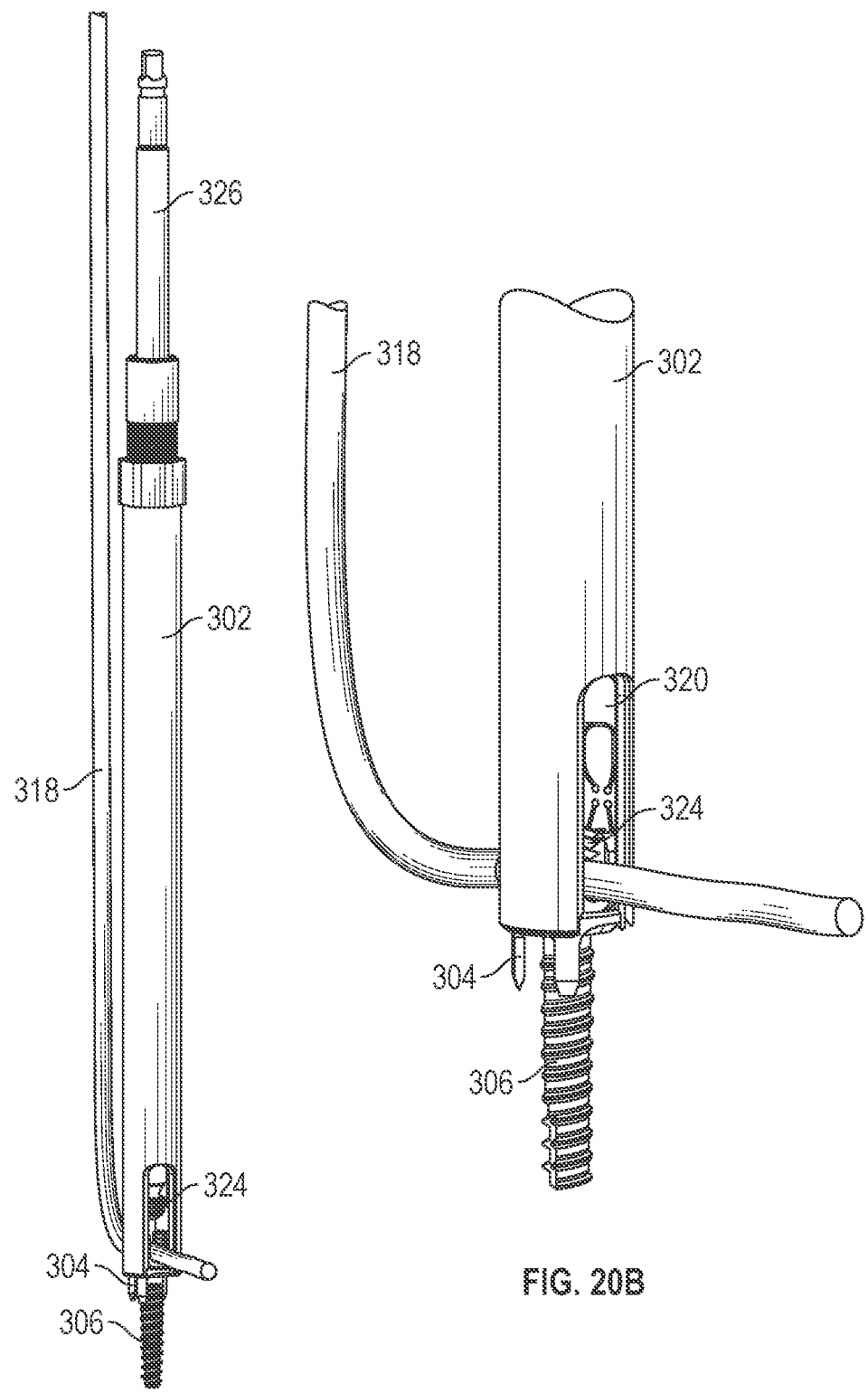
FIG. 20A is a perspective view of a system including the set screw inserter extending through the delivery device, in accordance with some embodiments.
FIG. 20B is a partial perspective view of the system including a set screw engaging the implant and cord.
Figure 23:
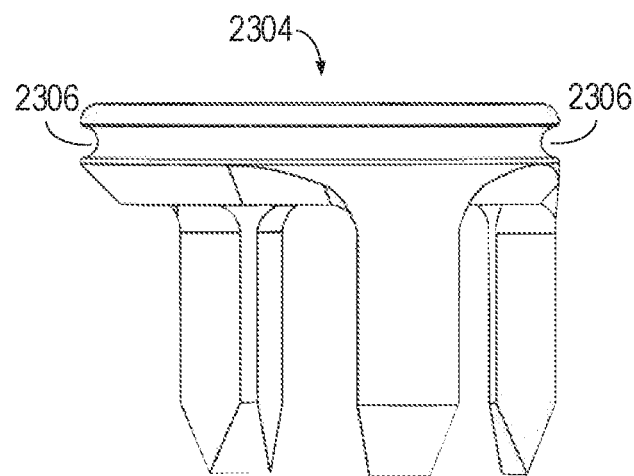
FIG. 23 is a perspective view of an annular anchor, in accordance with some embodiments.
Figure 24:
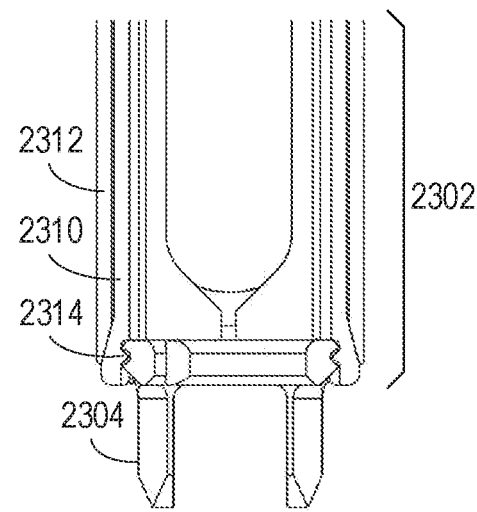
FIG. 24 is a side-view cross section of the annular anchor of FIG. 23 attached to a distal end of a corresponding delivery device, in accordance with some embodiments.
Figure 25:
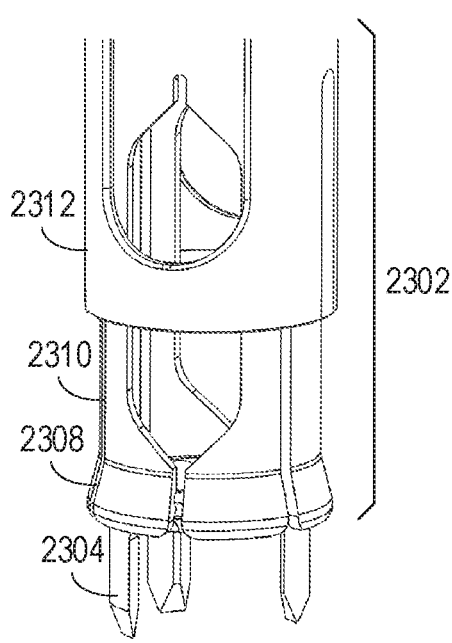
FIG. 25 is a perspective view of the annular anchor of FIGS. 23-24 attached to the distal end of the delivery device of FIG. 24, in accordance with some embodiments.
Figure 26:
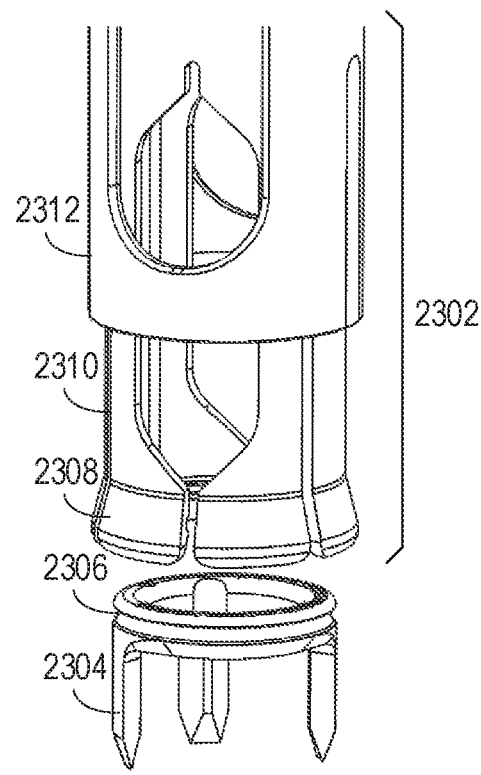
FIG. 26 is a perspective view of the annular anchor of FIGS. 23-25 detached from the distal end of the delivery device of FIGS. 24-25, in accordance with some embodiments.

The system 300 can include a delivery device 302 coupleable to an annular anchor 304 where the delivery device 302 facilitates delivery and implantation of the annular anchor 304. The system 300 can include an awl or a tap 314 insertable through a lumen extending through the delivery device 302 as shown in FIGS. 14-15. The awl or tap 314 can facilitate centering the anchor 304 as it contacts the bone prior to anchor insertion and, additionally or alternatively, can add stability to the delivery device 302. After the tap 314 is removed, an implant 306 can be coupled to the distal end of an implant inserter and the implant 306 delivered through the lumen via the implant inserter, then engaged in underlying bone as shown in FIGS. 16-17B. In an additional or alternative example, the delivery device 302 can be slotted at the distal end to facilitate insertion and reduction of a cord 318, as well as insertion of a set screw 324 as illustrated in FIGS. 18-22. In such examples and as shown in FIG. 18, the cord 318 can then be introduced through a slot 320 disposed in the distal end of the delivery device 302 that communicates with a receiving channel 322 disposed in a proximal end of the implant 306. A set screw 324 can be coupled to the distal end of a set screw inserter 326 and the set screw 324 delivered through the lumen via the set screw inserter 326, then provisionally docked in the receiving channel 322 of the implant 306. An auxiliary tool can also be provided that prevents rotation of the set screw 324 during subsequent reduction of the cord 318. In light of the present disclosure, a skilled artisan would appreciate that such an arrangement could be particularly useful for either the first or last implant in a series. In an additional or alternative example, as shown in FIGS. 21-22, the system can include multiple delivery devices 302, which can introduce multiple implants 306 connected to a same cord 318. Each implant 306 can be attached to the cord 318 with a respective set screw 324.

There are many possible mechanisms that can allow the anchor to attach and detach from the delivery device. It is beneficial to summary these mechanisms.

In the system 100 of FIG. 1, the annular anchor 104 and delivery device 102 of FIGS. 1-7 can be threadedly attached to one another, using mating screw threads on the annular anchor 104 and the delivery device 102. The delivery device 102 can detach from the annular anchor 104 by unscrewing the delivery device 102 from the anchor 104 (e.g., rotating the delivery device 102 about a longitudinal axis of the delivery device 102, while the anchor 104 remains stationary).

In the system 200 of FIGS. 8-13, the delivery device 202 can include biasable arms 222 that are biased to flex radially outward. To attach the anchor 204 to the delivery device 202, an outer sheath 228 can advance over the biasable arms 222 to force them radially inward. When forced radially inward, the biasable arms 222 engage a chamfered lip 224 of the anchor 204 and hold the anchor 204 against against the delivery device 202. To detach the anchor 204 from the delivery device 202, the outer sheath 228 can be retracted, so that the biasable arms 222 flex radially outward and release the chamfered lip 224 of the anchor 204.

The system 300 of FIGS. 14-22 can use either the threaded mechanism or the biasable arms mechanism to allow the anchor 304 to attach and detach from the delivery device 302.

FIGS. 23-26 show an additional example of an annular anchor 2304 and corresponding delivery device 2302, which can be used with any of the systems or system components shown in FIGS. 1-22, in accordance with some examples. The delivery device 2302 and the corresponding anchor 2304 differ from the earlier-described delivery devices and anchors in the manner in which the delivery device attaches to and/or detaches from the anchor.

The anchor 2304 can include a groove 2306 in an outer diameter of the anchor 2304. The groove 2306 can engage a corresponding feature on the delivery device 2302, in a manner similar to the chamfered lip 224 of the anchor 204 engaging the biasable arms 222 of the delivery device 202.

The delivery device 2302 can include a collet 2314 that can engage the groove 2306 of the anchor 2304. Discontinuous portions of the collet 2314 can be positioned on inward-facing surfaces of a plurality of fingers 2308. The fingers 2308 can be positioned at a distal end of an inner sleeve 2310, and can biased to flex radially outward.

To attach the anchor 2304 to the delivery device 2302, an outer sleeve 2312 can slide longitudinally (e.g., distally) over the inner sleeve 2310, so that an end of the inner sleeve 2310 can force the fingers 2308 radially inward, so that collet 2314 portions are forced into the groove 2306 of the anchor 2304. As long as the outer sleeve 2312 remains positioned over the fingers 2308, the collet 2314 remains forced into the groove 2306, and the anchor 2304 is held in place with respect to the delivery device 2302.

To detach the anchor 2304 from the delivery device 2302, the outer sleeve 2312 can retract longitudinally (e.g., proximally) over the inner sleeve 2310 away from the delivery device 2302, so that the fingers 2308 can expand radially outward, and the collet 2314 portions can disengage from the groove 2306 on the anchor 2304.

During use in a surgical procedure, the delivery device 2302 can optionally deliver one or more implants through the anchor 2304 to a target site in the patient, and can do so without damaging surrounding tissue. Instead of or in addition to the one or more implants, the delivery device 2302 can deliver the anchor 2304 itself to the target site in the patient. The delivery device 2302 can then detach from the anchor 2304, leaving the anchor 2304 and/or the one or more implants at the target site. The delivery device 2302 can then be removed from the patient, with the one or more implants and/or the anchor 2304 remaining at the target site.

FIG. 27 is a top view of an example of a handle 2700 suitable for use with any of the delivery devices of FIGS. 1-26. The primary purpose of the handle 2700 is to provide a surgeon or assistant with a quick connecting stabilizing device for use in stabilizing the delivery devices discussed above during intraoperative imaging (e.g., x-ray, fluoroscopy, and so forth). In the example of FIG. 27, the handle 2700 is shown as being removably engaged with the delivery device 102, but it can also removably engage with any of the delivery devices 202, 302, or 2302. The configuration of FIG. 27 is but one example of a handle; other suitable configurations can also be used.

The handle 2700 can be formed from a radiolucent material, such as plastic. The radiolucent material allows x-rays and other forms of radiation to pass through the handle 2700. By using the handle to grip a proximal portion of the delivery device 102, rather than gripping the delivery device 102 directly with his or her hand, the practitioner can ensure that his or her hand does not show up in an x-ray or other suitable image of the delivery device 102 and underlying implants.

The handle 2700 can include a distal portion 2702 that can at least partially surround a portion of the delivery device 102. In some examples, the distal portion 2700 can include a pair of opposing jaws 2704, which can be biased toward one another, and forced apart to engage the delivery device 102. In their disengaged state, the jaws 2704 can include an opening that is slightly smaller than a diameter of the delivery device 102.

In some examples, the handle 2700 can narrow in size at positions away from the jaws 2704. In some examples, the handle 2700 can expand to an expanded waist 2706. In some examples, the expanded waist 2706 can display a logo of the handle manufacturer.

In some examples, the handle 2700 can include a proximal portion 2708 that is grippable by the practitioner. In some examples, the handle 2700 can narrow in size at positions away from the proximal portion 2708 toward the expanded waist 2706. The exemplary handle illustrated in FIG. 27 can provide an instrument for stabilizing the delivery device during imaging. The handle is easy to connect and disconnect and will not affect the imaging. Any other instrument with similar capabilities could be used in a similar manner.

To further illustrate the device and related method disclosed herein, a non-limiting list of examples is provided below. Each of the following non-limiting examples can stand on its own, or can be combined in any permutation or combination with any one or more of the other examples.

In Example 1, a system can include: a delivery device including a distal end, a proximal end, and a lumen extending from the distal end to the proximal end; an annular anchor removably coupleable to the distal end of the delivery device, the anchor implantable at a target site in a patient via manipulation of the delivery device; the delivery device extendable outside the patient when the anchor is implanted at the target site; and an implant deliverable through the delivery device to the target site and implantable through the annular anchor, wherein the delivery device coupled to the annular anchor controls a trajectory of delivery of the implant into the target site In Example 2, the system of Example 1 can optionally be configured such that the delivery device is removable from the annular anchor subsequent to implantation of the implant.

In Example 3, the system of Examples 1 or 2 can optionally be further configured such that: the annular anchor includes a groove in an outer diameter of the annular anchor; the delivery device includes a collet configured to engage the groove and thereby removably attach the annular anchor to the delivery device; the collet is disposed on inward-facing surfaces of a plurality of fingers that are positioned at the distal end of the delivery device; the fingers are biased to flex radially outward; the delivery device includes an outer sleeve that is advanceable distally over the fingers to force the fingers radially inward and engage the collet into the groove; and the outer sleeve is retractable proximally from the fingers to allow the fingers to flex radially outward and disengage the collet from the groove.

In Example 4, the system of any one of Examples 1-3 can optionally, be configured such that the annular anchor includes threading disposed at a proximal end thereof, and wherein the distal end of the delivery device includes complementary threading for removably coupling to the threading of the annular anchor.

In Example 5 the system of any one of Examples 1-4 can optionally be configured such that at least a portion of the circumference of the annular anchor includes a chamfered lip extending inwardly from a proximal to a distal end of an annular portion of the annular anchor.

In Example 6, the system of any one of Examples 1-5 can optionally, be configured such that the delivery device includes a plurality of biasable arms for removably coupling the delivery device to the chamfered lip of the annular anchor.

In Example 7, the system of any one of Examples 1-6 can optionally be configured such that the annular anchor includes a staple.

In Example 8 the system of any one of Examples 1-7 can optionally, be configured such that the implant includes a fastener.

In Example 9, the system of any one of Examples 1-8 can optionally, be configured such that the fastener includes a screw or pedicle screw assembly.

In Example 10; the system of any one of Examples 1-9 can optionally be configured such that the fastener includes a head including an upwardly extending pair of arms defining a receiving channel.

In Example 11, the system of any one of Examples 1-10 can optionally be configured such that the system further includes a set screw threadedly receivable in the receiving channel, the set screw being positioned within the receiving channel to secure a flexible member therein upon advancement of the set screw within the receiving channel.

In Example 12, the system of any one of Examples 1-11 can optionally further include a radiolucent handle configured to removably engage a proximal portion of the delivery device.

In Example 13, a method can include: removably coupling a delivery device to an anchor; inserting the anchor into a target delivery site on a patient, the anchor positioned to control location and trajectory of an implant; delivering the implant through the delivery device; securing the implant to underlying tissue; and decoupling the delivery device from the annular anchor and removing the delivery device over the implant.

In Example 14, the method of Example 13 can optionally be configured such that subsequent to removably coupling the delivery device to the anchor, the delivery device is used to implant the anchor into underlying tissue.

In Example 15, the method of any one of Examples 1314 can optionally be configured such that the anchor is an annular anchor and inserting the anchor into the target delivery site includes inserting the implant through the annular anchor.

In Example 16, the method of any one of Examples 13-15 can optionally be configured such that annular anchor includes a staple and inserting the anchor into the target delivery site includes inserting a staple into the target delivery site.

In Example 17, the method of any one of Examples 13-16 can optionally be configured such that securing the implant includes securing a fastener to underlying tissue.

In Example 18, the method of any one of Examples 13-17 can optionally be configured such that the fastener includes a head including an upwardly extending pair of arms defining a receiving channel and further including inserting an elongate member into the receiving channel In Example 19, the method of any one of Examples 13-18 can optionally further include threadedly securing a set screw in the receiving channel, wherein threadedly securing the set screw further includes advancing the set screw in the receiving channel to secure the elongate member therein.

In Example 20, the method of any one of Examples 13-19 can optionally be configured such that the anchor is repositionable prior to delivering the implant through the delivery device.

The above Detailed Description includes references to the accompanying drawings, which form a part of the Detailed Description. The drawings show, by way of illustration, specific configurations in which the embodiments can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more," In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the embodiments should be determined with reference to the appended claims, along with the full scope of equivalents to which such claims are entitled.

In the foregoing Detailed Description, the method and apparatus of the present disclosure have been described with reference to specific embodiments thereof. It will, however, be evident that various modifications and changes may be made thereto without departing from the broader spirit and scope of the present disclosure. The present specification and figures are accordingly to be regarded as illustrative rather than restrictive.

What is claimed is:

1. An annular anchor comprising:
   a circular body surrounding a central bore and including an implant instrument interface along an edge of an outer circumference, wherein the instrument interface includes a downward-facing chamfered lip positioned on a lower side of the circular body along at least a portion of the outer circumference, wherein the downward-facing chamfered lip is a sloped transition surface between the edge of the outer circumference and an edge of a substantially planar surface through which the central bore passes; and
   a plurality of spikes extending from a distal side of the circular body, wherein at least one spike of the plurality of spikes includes an exterior surface of a first width, an opposite interior surface of a second, different width, and at least one sloped transition surface connecting the exterior surface and the opposite interior surface, and wherein a distal portion of the at least one spike of the plurality of spikes includes at least one quadrilateral-shaped surface.

2. The annular anchor of claim 1, wherein the downward-facing chamfered lip is positioned on at least a portion of the edge of the outer circumference.

3. The annular anchor of claim 2, wherein the downward-facing chamfered lip extends inwardly from a proximal end to a distal end of an annular portion of the annular anchor, wherein the proximal end is an upper side of the annular portion of the annular anchor, and wherein the distal end is the lower side of the annular portion of the annular anchor.

4. The annular anchor of claim 1, wherein the bore in the circular body is adapted to receive a bone screw through a delivery device attached to the instrument interface.

5. The annular anchor of claim 1, wherein the plurality of spikes are unevenly distributed around the outer circumference of the annular anchor.

6. The annular anchor of claim 5, wherein two non-adjacent spikes of the plurality of spikes define a plane separating the annular anchor into a first portion and a second portion, wherein the plurality of spikes are unevenly distributed around the outer circumference of the annular anchor such that additional spikes of the plurality of spikes are positioned around the outer circumference only in the first portion of the annular anchor separated by the plane.

7. A system comprising:
an elongate delivery device comprising a distal end, a proximal end, and a lumen extending from the distal end to the proximal end, the distal end including an anchor interface;
an annular anchor comprising:
 a circular body surrounding a central bore and including an instrument interface along an edge of an outer circumference, wherein the instrument interface includes a downward-facing chamfered lip positioned on a lower side of the circular body along at least a portion of the outer circumference, wherein the downward-facing chamfered lip is positioned along at least a portion of the edge of the outer circumference and extends inwardly from a proximal end that is proximate to a top surface of the circular body to a distal end positioned underneath a top surface; and
 a plurality of spikes extending from a distal side of the circular body,
 wherein the downward-facing chamfered lip is a sloped transition surface between the edge of the outer circumference and an edge of a substantially planar surface through which the central bore passes,
 wherein the annular anchor is removably coupleable to the anchor interface of the delivery device via the instrument interface, and wherein the anchor interface includes a plurality of biasable arms and at least one side portion positioned between adjacent biasable arms of the plurality of biasable arms, each biasable arm including a distal end adapted to engage the downward-facing chamfered lip; and
an implant deliverable through the delivery device and implantable through the annular anchor.

8. A system comprising:
a cylindrical delivery device comprising a distal end, a proximal end, and a lumen extending from the distal end to the proximal end, the distal end including an anchor interface;
an annular anchor comprising:
 a circular body with a top surface that is substantially circular and planar, wherein the top surface surrounds a central bore, wherein the circular body includes an instrument interface at a proximal end of the circular body, the instrument interface being positioned at the proximal end along an outer circumference of the circular body; and
 a plurality of spikes extending from a distal side of the circular body, wherein an exterior surface of at least one spike of the plurality of spikes is at the outer circumference of the circular body,
wherein the annular anchor is removably coupleable to the anchor interface of the delivery device via the instrument interface, wherein the instrument interface includes one of: a downward-facing chamfered lip positioned on a lower side of the circular body and extending inwardly from a proximal end that is proximate to the top surface of the circular body to a distal end positioned underneath the top surface, and wherein the anchor interface includes a plurality of biasable arms and at least one side portion positioned between adjacent biasable arms of the plurality of biasable arms, each biasable arm including a distal end adapted to engage the downward-facing chamfered lip; and
an implant deliverable through the delivery device and implantable through the annular anchor.

9. The system of claim 8, wherein the anchor interface includes a circular cross-sectional shape while coupled to the instrument interface.

* * * * *